(12) United States Patent
Schechter et al.

(10) Patent No.: US 7,670,843 B2
(45) Date of Patent: Mar. 2, 2010

(54) POLYMERIC FILM SENSOR FOR POLYCYCLIC AROMATIC HYDROCARBONS

(75) Inventors: Israel Schechter, Haifa (IL); Chanan Sluszny, Shimshit (IL); Valery Bulatov, Nesher (IL); Vladimir Gridin, Yokneam (IL)

(73) Assignee: Technion Research and Development Foundation Ltd., Haifa (IL)

( * ) Notice: Subject to any disclaimer, the term of this patent is extended or adjusted under 35 U.S.C. 154(b) by 903 days.

(21) Appl. No.: 10/548,068

(22) PCT Filed: Mar. 4, 2004

(86) PCT No.: PCT/IL2004/000221

§ 371 (c)(1),
(2), (4) Date: Sep. 6, 2005

(87) PCT Pub. No.: WO2004/079330

PCT Pub. Date: Sep. 16, 2004

(65) Prior Publication Data

US 2006/0183239 A1    Aug. 17, 2006

(51) Int. Cl.
 *G01N 33/00* (2006.01)
(52) U.S. Cl. .................. 436/140; 436/139; 436/146; 436/172; 436/805
(58) Field of Classification Search .................. None
See application file for complete search history.

(56) References Cited

U.S. PATENT DOCUMENTS 3,619,344 A * 11/1971 Wolinski et al. ......... 428/314.4

3,774,623 A * 11/1973 Merrill ......... 131/352

OTHER PUBLICATIONS

Brown, R. Stephen, et al., Coupling of Solid Phase Micro-Extraction Film to Optical Fibers for On-line Detection of Polycyclic Aromatic Hydrocarbons by Laser Induced Fluorescence, 1998, EnviroAnalysis, p. 441-446.*
Wright, John D., et al., Development of a iezo-optical chemical monitoring system, 1998, Sensors and Actuators, vol. B51, pp. 121-130.*
Fisher, Michel, et al. Fast Aerosol Analysis by Fourier Transform Imaging Fluorescence Microscopy, 1998, Analytical Chemisry, vol. 70, pp. 2409-2414.*
IARC, Vinyl Chloride, Polyvinyl chloride and Vinyl Chlor, 1979, IARC Monograph on the evaluation of the carcinogenic risk of chemicals to humans, vol. 19, pp. 377-438.*
GH Vickers et al. Anal Chim. Acta 1987, 192, 145-153; "Time-Resolved Flourescence with an Optical Fiber Probe".
JD Winefordner (Editor). "*Air Monitoring by Spectroscopic Techniques*"; Chemical Analysis vol. 27; New York : Wiley, c1994.
T Vo-Dihn (Editor). "*Chemical Analysis of Polycyclic Aromatic Compounds*" ; Chemical Analysis vol. 101; New York : Wiley, © 1989.

* cited by examiner

*Primary Examiner*—Elena G. Gakh
*Assistant Examiner*—Robert Xu
(74) *Attorney, Agent, or Firm*—Mark M. Friedman

(57) ABSTRACT

A method of and device for sampling polycyclic aromatic hydrocarbons (PAHs) in the ambient environment, the method including: (a) providing a polymer film for collecting the PAHs; (b) exposing the polymer film to a gas containing the PAHs, and (c) performing an analysis of the PAHs collected by the polymer film, the analysis being selected from the group consisting of fluorescence analysis and Fourier Transform Imaging Microscopy (FT-SIM).

9 Claims, 10 Drawing Sheets

The worker is shown wearing the proposed badge to determine his exposure to chemical hazards durinh one entire work shift.

7A

7B

7C

7D

7E

FIG. 8A
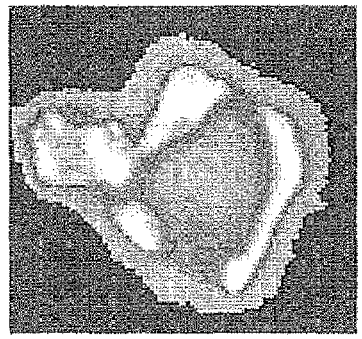
FIG. 8B
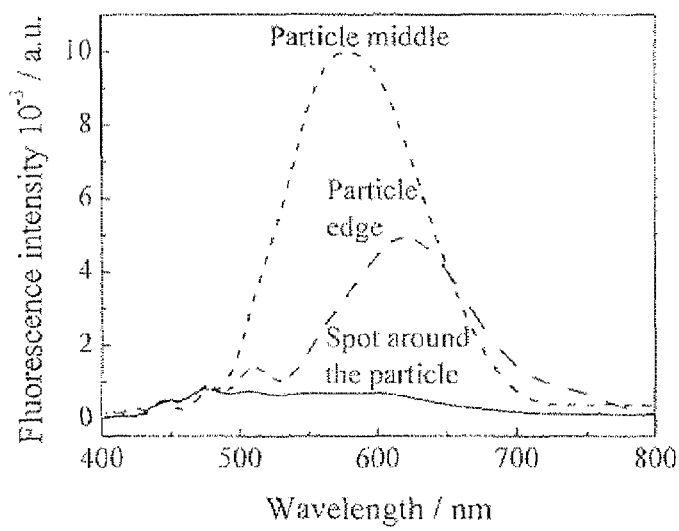
FIG 8C
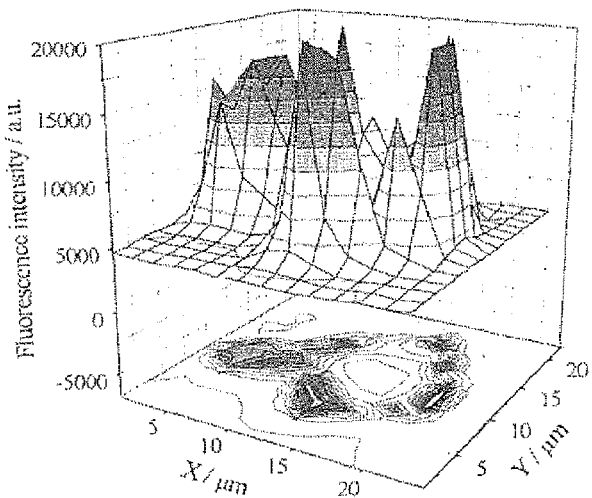
FIGS. 8A-8C

POLYMERIC FILM SENSOR FOR POLYCYCLIC AROMATIC HYDROCARBONS

FIELD AND BACKGROUND OF THE INVENTION

The present invention relates to a device and method for monitoring exposure to chemicals and pollutants, and more particularly, to a portable device for, and method of, accumulating chemicals and pollutants that are present in an ambient environment.

Polycyclic Aromatic Hydrocarbons (PAHs) are formed by the incomplete combustion of organic matter, and many of the compounds are known as carcinogens and/or mutagens. PAHs are found in the atmosphere in both gaseous and particulate states. Light (3-ring and 4-ring) PAHs occur primarily in the vapor phase, heavy ($\geq$6-ring) PAHs are found predominantly in a particulate form, and 5-ring PAHs are commonly present in the vapor phase or as particulate matter. Temperature variations can promote a phase transition to either a gaseous state or a particulate state of various PAH species.

Prior-art techniques for sampling of vapor phase PAHs include removing PAHs from the air by solid cyclic oligosaccharides such as cyclodextrins, adsorption on an organic polymer (e.g., polyurethane foams) or on inorganic sorbents (silica gel or alumina), or cryogenic trapping. Extraction, chromatographic separation and optical detection follow the sampling [see *Chemical Analysis of Polycyclic Aromatic Compounds*, Vo-Dinh, T., ed., Wiley, N.Y. (1989)]. Effective extraction of PAH traces from the sampler is complex. Sample reduction in handling, incomplete extraction, and irreversible adsorption are known potential loss mechanisms for PAH compounds during the sample preparation step [see M. W. Sigrist, "Air Monitoring by Spectroscopic Techniques", in: *Chemical Analysis*, J. D. Winefordner, ed., Wiley, N.Y. (1994)].

The monitoring of PAHs in the ambient air is a well-developed field in the U.S., Europe, and other industrialized areas. In particular, the monitoring of worker exposure to PAHs in the ambient air of the workplace is commonplace. A prevalent device for monitoring the exposure to chemicals is shown in FIG. 1A. The device includes a sorbent tube 10, a personal air pump 12, which is typically fastened to a belt, and a connecting tube 14 providing fluid communication between sorbent tube 10 and personal air pump 12. Personal air pump 12 draws ambient air through sorbent tube 10, which contains an active material for retaining various PAHs present in the ambient air.

Personal air pump 12 accompanies the worker throughout his entire work shift, in compliance with OSHA requirements. Personal air pump 12 is bulky (typically ~14×12×5 cm), heavy (~1 kg), and somewhat noisy. Consequently, such units are discomforting to wear, and are often used only when severe problems are indicated.

Moreover, the prior-art devices are costly, and the analytical techniques are both complicated and expensive. The cost of a typical pump is about $300, and each disposable sorbent tube costs about $2. The chemical analysis of each sorbent tube may take between 30 to 120 minutes, and requires a trained analyst. The instrumentation must be routinely calibrated, and a trained technician is required for ensuring proper sampling.

Extraction, chromatographic separation and optical detection follow the sampling stage. Such separate sampling and detection procedures result in numerous errors in estimating the contamination level.

Recently, particulate pollutants have been identified as extremely potent carcinogens and/or mutagens. The emission of particulate PAH traces into the atmosphere is a subject of growing concern. It will be appreciated by one skilled in the art that sorbent tubes are do not provide an adequate solution for the sampling of aerosols and particulate pollutants.

There is therefore a recognized need for, and it would be highly advantageous to have, a portable device for, and method of, monitoring chemicals and pollutants present in the ambient environment, which overcome the manifest deficiencies of the prior art. It would be of particular advantage to have a device that is light and compact, robust, inexpensive, and provides accurate results. Finally, it would be highly advantageous to have a device that is suited for the sampling of aerosols and particulate pollutants.

SUMMARY OF THE INVENTION

The present invention is a portable device for, and method of, monitoring chemicals and pollutants present in the ambient environment.

According to the teachings of the present invention there is provided a method of sampling and analyzing polycyclic aromatic hydrocarbons (PAHs) in the ambient environment, the method including the steps of: (a) providing a polymer film for collecting the PAHs; (b) exposing the polymer film to a gas containing the PAHs, and (c) performing an analysis of the PAHs collected by the polymer film, the analysis being selected from the group consisting of fluorescence analysis and Fourier Transform Spectral Imaging Microscopy (FT-SIM).

According to yet another aspect of the present invention there is provided a polymeric-film device for sampling polycyclic aromatic hydrocarbons, the device including: a polymeric film for exposing to a gas containing at least one polycyclic aromatic hydrocarbon (PAH), the polymeric-film designed so as to be transparent with respect to at least one PAH.

According to further features in the described preferred embodiments, the analysis of the PAHs is a direct analysis.

According to still further features in the described preferred embodiments, the polymer film for collecting the PAHs is a transparent polymer film.

According to still further features in the described preferred embodiments, the PAHs include particulate PAHs.

According to still further features in the described preferred embodiments, the PAHs form an aerosol with the gas.

According to still further features in the described preferred embodiments, the polymer film is produced from poly (vinyl chloride-co-vinyl acetate) prior to step (a).

According to still further features in the described preferred embodiments, the poly(vinyl chloride-co-vinyl acetate) contains at least 70% vinyl chloride.

According to still further features in the described preferred embodiments, the analysis includes fluorescence analysis.

According to still further features in the described preferred embodiments, the analysis includes FT-SIM.

According to still further features in the described preferred embodiments, the method further includes the step of: (d) configuring the polymer film as a portable sampling device for wearing by a subject being exposed to a particular environment.

According to still further features in the described preferred embodiments, the portable sampling device is configured as a badge for fastening to clothing of the subject.

According to still further features in the described preferred embodiments, the badge has a surface area for collecting the PAHs, the surface area being less than 50 square centimeters.

According to still further features in the described preferred embodiments, the badge has a surface area for collecting the PAHs, the surface area being less than 30 square centimeters.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 8A is a FT SIM image of a large perylene particle (225 μm2);

FIG. 8B shows fluorescence spectra measured at the central part of the particle, at the particle edge, and of the spot around the particle;

FIG. 8C is a 3D-plot of the wavelength-integrated fluorescence intensity corresponding to FIG. 8A;

DESCRIPTION OF THE PREFERRED EMBODIMENTS

Figure 1A:
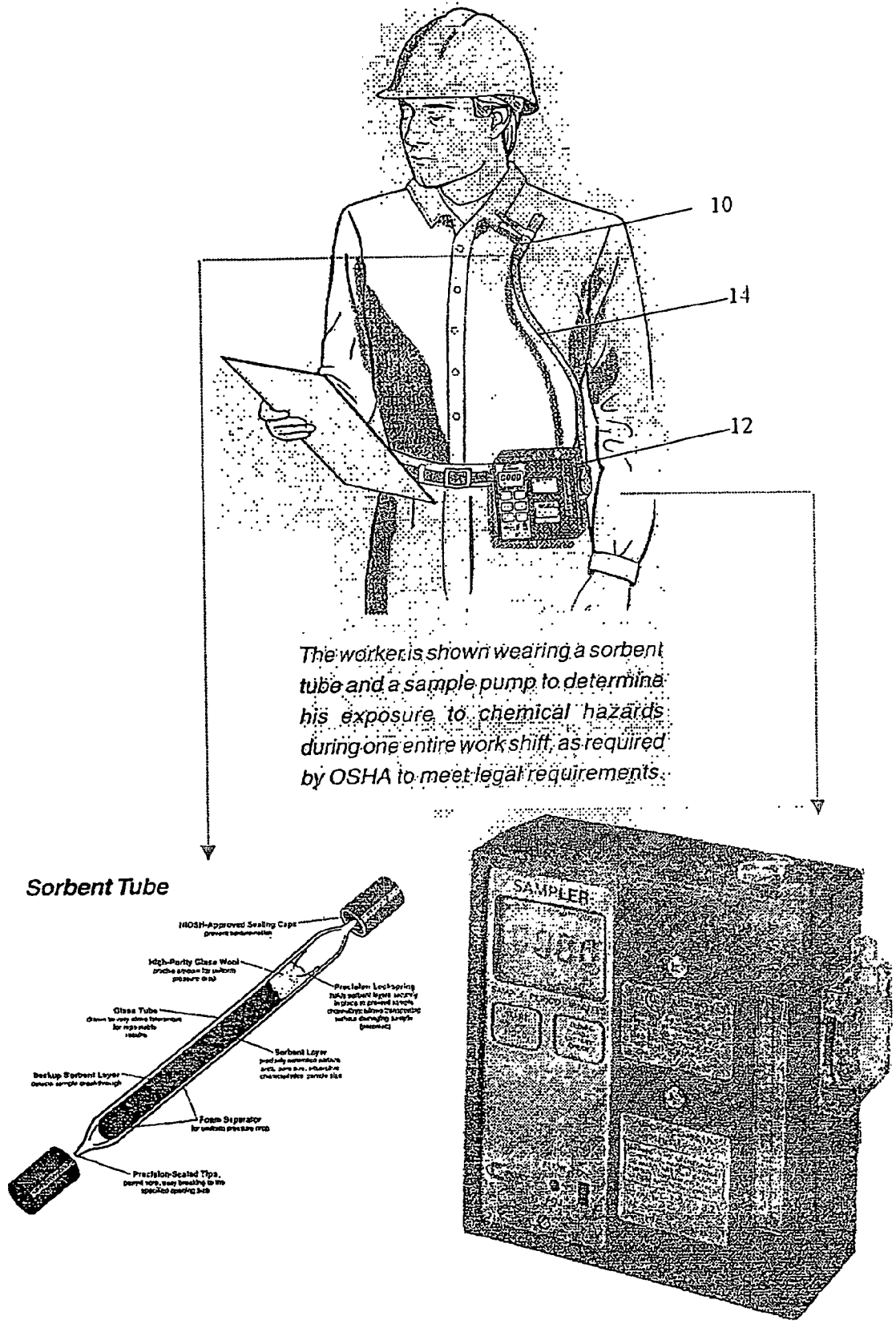
FIG. 1A shows a prior-art device for sampling chemicals in the environment.

The present invention is a portable device for, and method of, monitoring chemicals and pollutants present in the ambient environment.

The principles and operation of the device and method of the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

Figure 1B:
FIG. 1B shows a device for sampling chemicals in the environment, according to the present invention.

The present invention provides for airborne volatile PAH analysis using polymer film sampling and direct fluorimetric measurement. An exemplary device for sampling the exposure to chemicals in the environment, according to the present invention, is provided schematically in FIG. 1B. Instead of a prior-art sampling system including sorbent tube 10, personal air pump 12, and connecting tube 14 (see FIG. 1A), the inventive device consists of a polymer sampling card 20. The function of polymer sampling card 20 will be described in greater detail hereinbelow.

Fluorimetry is known to be a particularly sensitive method for PAH detection [see G. H. Vickers, et al., *Anal. Chim. Acta*, 1987, 192, 145-153]. We have found that certain polymeric films readily entrap PAH vapors (gaseous phase) and, therefore, can be monitored by fluorimetric measurements. It should be noted that other materials absorbing PAHs do exist (for example, activated carbon, silica, alumina and yeast). These materials are usually non-transparent, which limits their suitability to on-line measurements. Moreover, compared to polymer films, extraction of PAHs from such materials is considerably more complex.

The exemplary target materials for the analysis were naphthalene, pyrene and perylene, which possess different physical and spectral properties. Commercially-available naphthalene (Baker, 99%), pyrene (Aldrich, 99%) and perylene (Aldrich, 99.5%) were used without further purification. Stock solutions of PAHs (100 ppm) were prepared using acetonitrile. Variable PAH concentrations were obtained by subsequent serial dilution in acetonitrile.

The solvents used include acetone (BioLab Ltd., Israel), tetrahydrofuran—THF BioLab Ltd., Israel) and acetonitrile (Baker). All solvents were analytical grade or HPLC grade, so as to avoid any background effects due to impurities.

The polymer film was prepared as follows: poly(vinyl chloride-co-vinyl acetate) containing approximately 90% vinyl chloride was dissolved in THF in a 1:6 to 1:12 ratio of polymer powder to THF. The THF was cooled, and the poly (vinyl chloride-co-vinyl acetate) was slowly added, while stirring. After complete dissolution was accomplished and a clear and homogeneous solution was obtained, phthalic acid bis(2-ethyl-hexyl ester) was added as a softening agent in a 1:1.5 to 1:3 ratio of softener to polymer powder. The resulting polymer solution was placed on a flat glass surface and polymerized at ambient pressure at 80° C. The polymer film formed on the surface was gently separated from the glass support and samples of a suitable size were sliced.

Fluorescence spectra of PAHs were obtained using a commercially-available device (SLM AMINCO BOWMAN). The PAHs containing polymer bands were placed on a non-reflectance surface and analyzed using a front surface measurement accessory. The PAHs solutions were measured into a quartz 10×10×45 mm cuvette. Excitation was performed at 275, 335 and 408 nm for naphthalene, pyrene and perylene, respectively. Fluorescence intensities were calculated while integrating the corresponding spectra.

The PAH vapor absorption experiments were carried out using 30×60 mm boxes containing saturated PAHs vapors produced by sublimation of PAHs crystals placed at the bottom of the box. The polymer film bands were arranged onto the glass slides fixed in the middle of each box. The PAH-contaminated films were extracted three times with 1.5 ml of acetonitrile. The extraction efficiency was 95-98%.

Figure 2A:
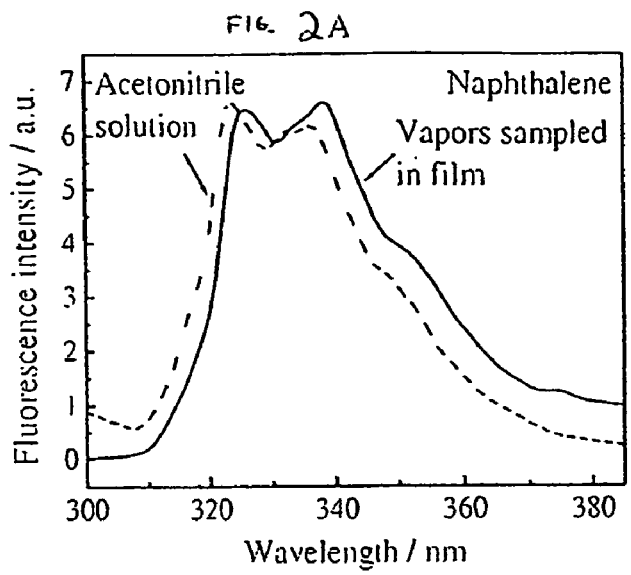
FIGS. 2A-2C are comparative plots of fluorescence emission spectra of naphthalene (FIG. 2A), pyrene (FIG. 2B), and perylene (FIG. 2C), dissolved in a polymer film, vs. the same materials dissolved in acetonitrile.
Figure 2B:
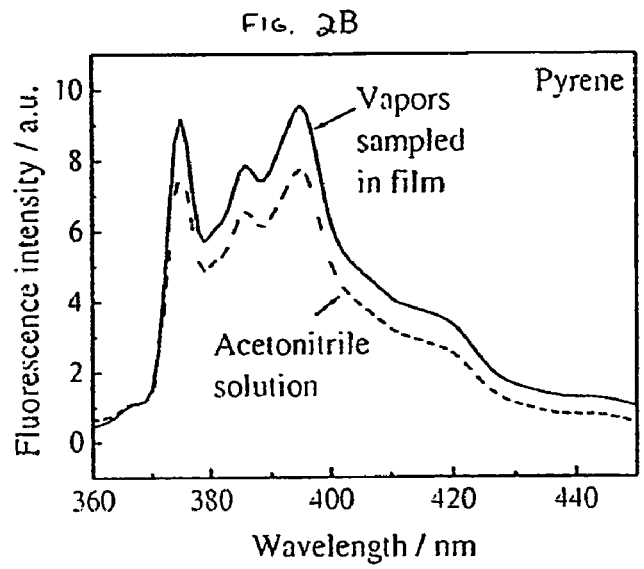
Figure 2C:
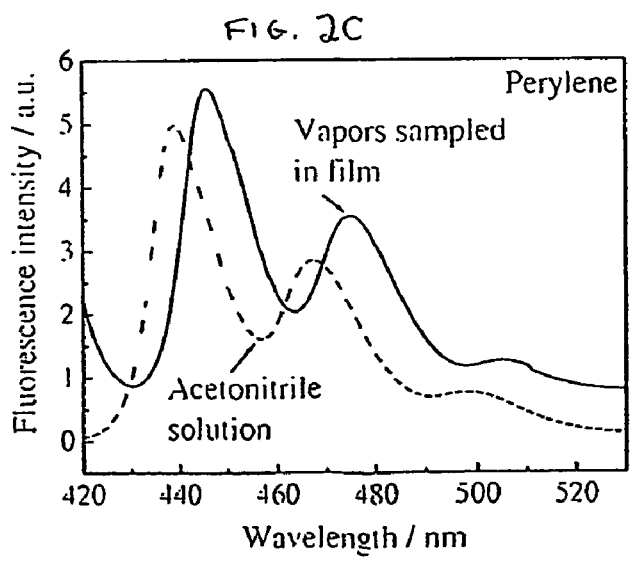

In the exemplary tests described herein, the target materials (for analysis) were saturated naphthalene, pyrene and perylene vapors. Referring now to the drawings, FIGS. 2A-2C show fluorescence emission spectra of a polymer film loaded with PAHs (naphthalene, pyrene and perylene, respectively) compared to fluorescence emission spectra of an acetonitrile solution containing these PAHs.

The fluorescence emission spectra of the organic extracts of the polymer film sensor (OE-PFS) were found to be similar to those obtained with standard solutions (spectra not provided). In the case of pyrene, the fluorescence emission spectra, obtained upon direct illumination of the film and those from OE-PFS, are almost identical in terms of the shape and peak positions.

The spectra of naphthalene and perylene obtained in the case of direct illumination of polymeric film are in good agreement with solution spectra, excluding the peak location. The peaks in the film spectra are simply shifted to the longer wavelengths.

These shifts of in-situ fluorescence spectra might, at first, be attributed to the matrix polarity effects. The polymer matrix is considered as a non-polar solvent for the PAHs. The effect of solvent polarity on molecule emission is known. It is also known that while pyrene fluorescent characteristics are strongly dependent on solvent polarity, those of perylene remain constant, regardless of solvent polarity. Here we observe an opposite effect: there is no difference between solution and polymer spectrum for pyrene, while a shift to longer wavelengths is viewed for naphthalene and perylene. In addition, non-polar solvents usually cause a blue shift. It can be concluded, therefore, that the spectral changes are associated with factors other than a matrix polarity.

Figure 3:
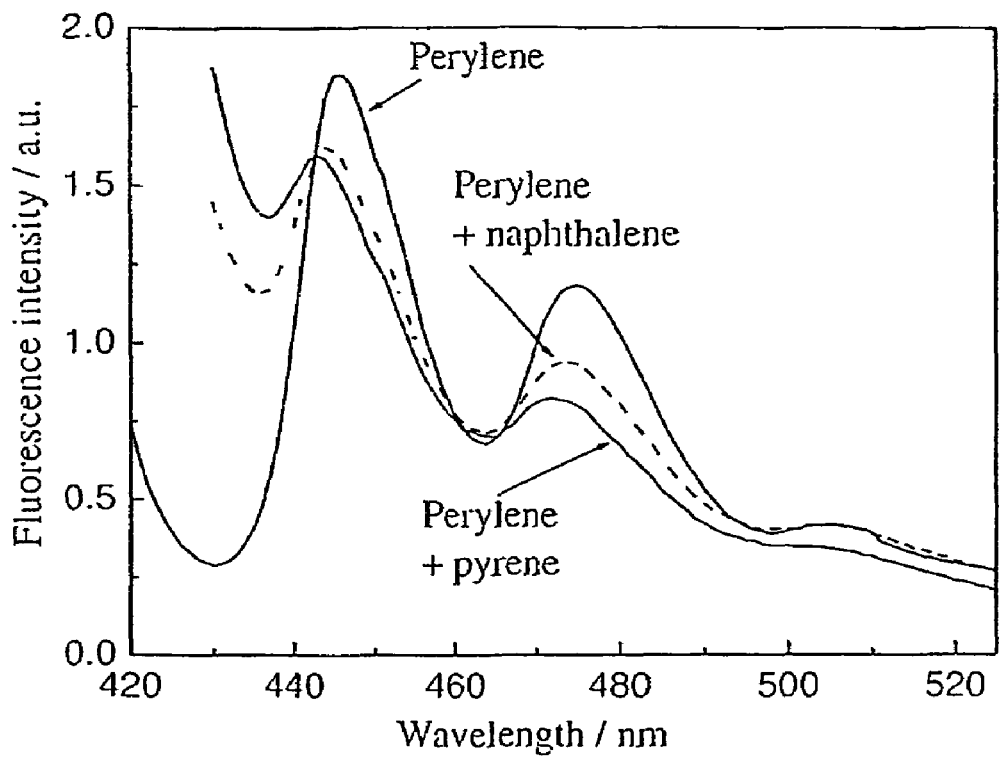
FIG. 3 is a plot of the fluorescence emission spectrum of perylene, sampled in the polymer film, in the presence of pyrene and naphthalene.

A plot of the fluorescence emission spectrum of perylene collected in the polymer film, in the presence of pyrene and naphthalene, is provided in FIG. 3.

Figure 4:
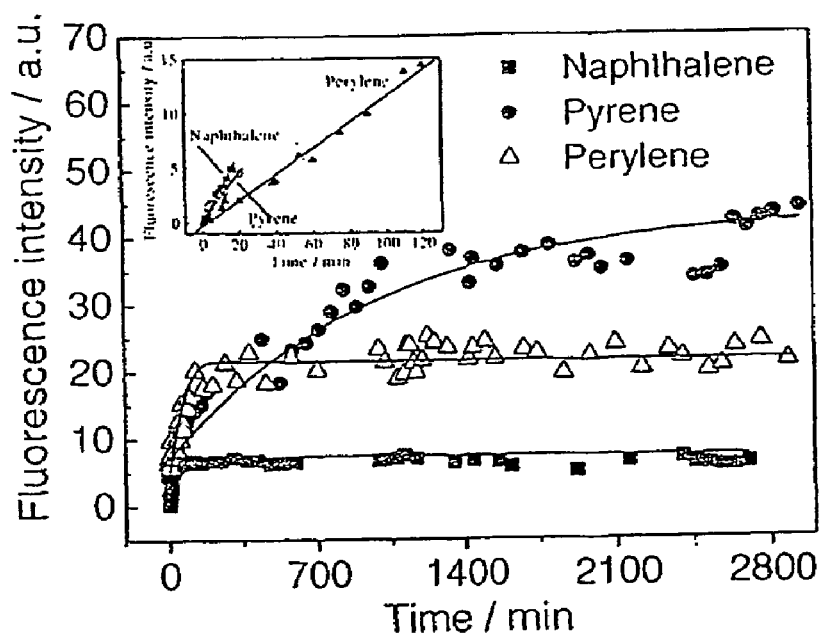
FIG. 4 show plots of the fluorescence emission intensity of naphthalene, pyrene, and perylene vapors, sampled in the polymer film, as a function of sampling time.

The adsorption of PAH vapors into the inventive polymer film was investigated at ambient conditions to characterize the dynamic range for direct fluorimetric measurements. Polymer films were exposed to naphthalene, pyrene and perylene vapors for various periods of time. FIG. 4 depicts the fluorescence intensity as a function of exposure time for naphthalene, pyrene and perylene. It can be seen that the response time of the sensor is on the order of minutes. According to the data presented in FIG. 4, the minimal exposure times within a 95% confidence interval are 0.5, 3, and 7 minutes for naphthalene, pyrene, and perylene, respectively. The fluorescence increases linearly up to 16, 20, and 120 minutes for naphthalene, pyrene, and perylene, respectively, the slopes of the linear curves being 0.29, 0.20, and 0.10. Distinction in entrapping rates of PAH vapors can be explained by a difference in sublimation vapor pressures of naphthalene, pyrene, and perylene, influencing vapor adsorption. While naphthalene is highly sublimated even at room temperatures, the sublimation of pyrene and perylene is known to be slower.

Saturation is observed in the fluorescence measurements. The saturation may be caused by self-absorption or some quenching within a polymer layer or by the limited number of sites in the film. A reliable calibration step is needed for the evaluation of the constancy of the analyte and detection limits. For this purpose, known amounts of pyrene and perylene standard solutions were introduced onto film slides having a known area.

Figure 5:
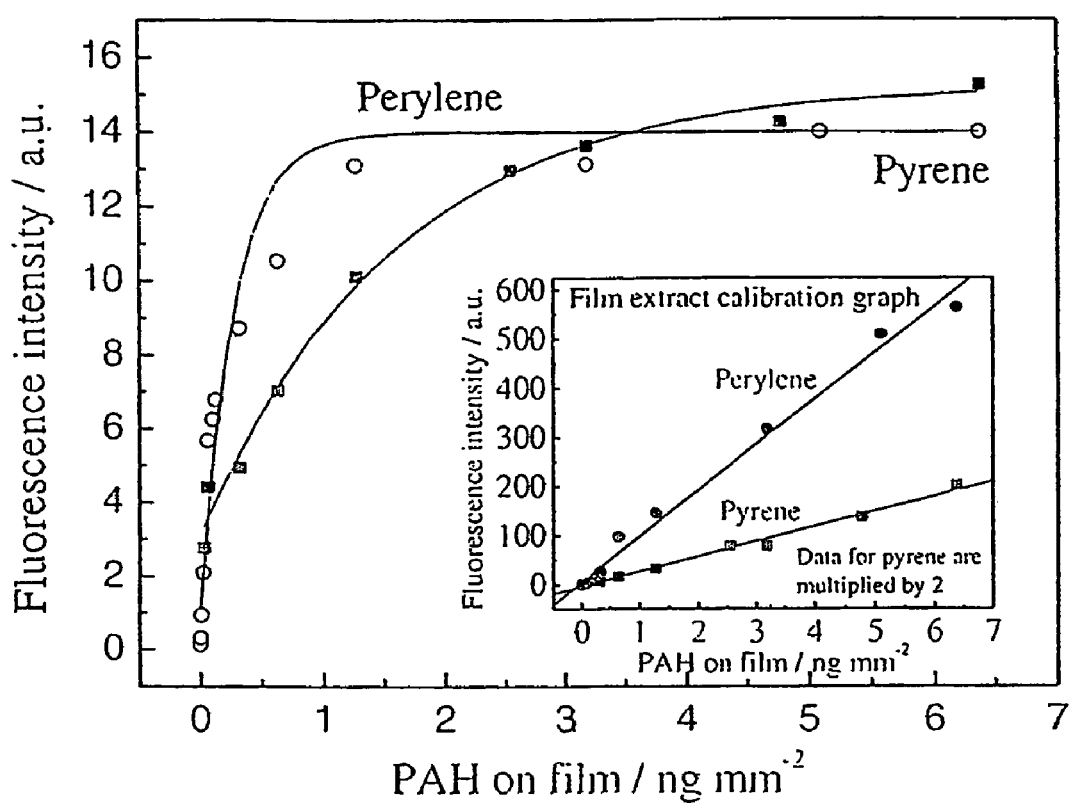
FIG. 5 is a plot of the fluorescence intensity of pyrene and perylene on polymer film as a function of concentration.

After evaporation of the solvent, the fluorescence of the films was measured. Subsequently, the film slides were extracted and the fluorescence intensity of the obtained solutions measured. The data were compared to the fluorescence measurements carried out with standard PAH solutions. The calibration graphs for the film slides and the OE-PFS, are shown in FIG. 5 and in the inset thereof.

The directly-measured fluorescence on the polymer film increases linearly with concentration up to 1.3 ng mm$^{-2}$ for pyrene and up to 0.07 ng mm$^{-2}$ for perylene. The fluorescence measured in OE-PFS increases linearly with concentration in the investigated range (up to 6.5 ng mm$^{-2}$ of the film), which indicates that the observed saturation (see FIG. 5) is due to self-adsorption within the thin film "cuvette" and is not caused by the overload of the film by the analyte. Detection limits on the order of pg mm$^{-2}$ for perylene and on the order of $\frac{1}{10}$ μg mm$^2$ for pyrene are possible.

The difference between the detection limits may be attributed to various fluorescence properties of the PAHs. For example, the quantum yields in cyclohexane solution are 0.65 and 0.87 for pyrene and perylene, respectively. In addition, the structure and physical properties of PAHs influence their affinity to the polymer film matrix, as described hereinabove.

An important characteristic of the PAH-loaded polymer film is the stability of the fluorescence signal with time. Since the fluorescence intensity is a function of PAH concentration, desorption of entrapped compounds from the film causes a decrease in the measured signal. The possibility of using stored film makes the technique more attractive. The stability of the PAH-contaminated films, stored for several days in open vessels at ambient conditions, was tested. The fluorescence intensity was measured as a function of time.

It was found that naphthalene fluorescence drops within three hours to the background level, hence, the desorption of naphthalene from the film surface is manifest. The fluorescence response of pyrene and perylene was measured for samples exposed to PAHs vapors for 5 minutes (the fluorescence output of such samples lies in the linear detection range) and for approximately 2 days (here the fluorescence measurements are distorted by self-absorption).

Pyrene and perylene measurements indicate an increase in measured fluorescence emission at the beginning of the experiment and constant fluorescence in all following measurements. This can be explained by the increase of diffusion of PAHs from the film surface caused by the change in ambient conditions (transferring from closed box to open air). The film is transparent and fluorescence emission from PAHs dissolved into the film molecules is detected.

However, molecules of the upper layer scatter the light and the measured emission signal decreases. The diffusion of the upper molecular layer from the film surface causes a decrease of self-absorption and, consequently, increases the fluorescence signal of PAH molecules dissolved into the film. It can be concluded that the film sensor is substantially irreversible for pyrene and perylene measurements. Thus, the polymer film is quite suitable for off-line experiments in the case of compounds having low volatility. It also follows that highly-volatile substances such as naphthalene are not suitable for long-term measurements.

The suitability of the present invention for quantifying gaseous mixtures of PAHs was also demonstrated experimentally. The target materials were mixtures of naphthalene with pyrene or perylene, and pyrene with perylene. Fluorescence was measured at fixed time intervals over a period of 10 minutes. The bands of the PAHs in the given mixtures were spectrally resolved. The signals of the PAHs were measured at typical wavelengths.

Figure 6A:
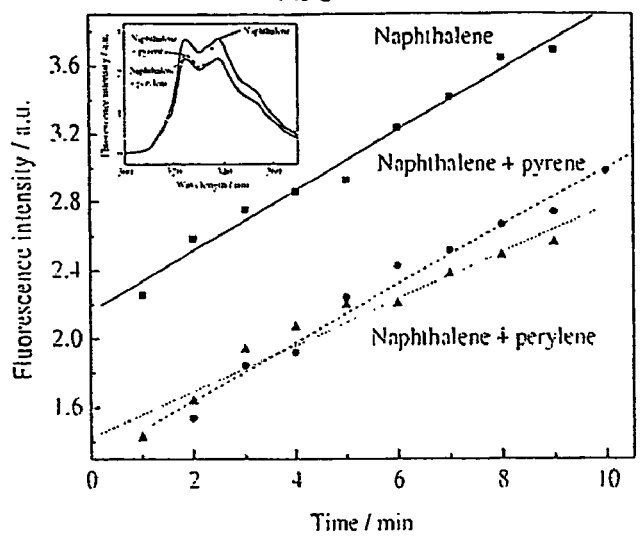
FIGS. 6A-6C show the fluorescence emission intensity of naphthalene and pyrene (6A), naphthalene and perylene (6B), and pyrene and perylene (6C) mixtures as a function of time compared with fluorescence emission intensities of naphthalene, pyrene and perylene.
Figure 6B:
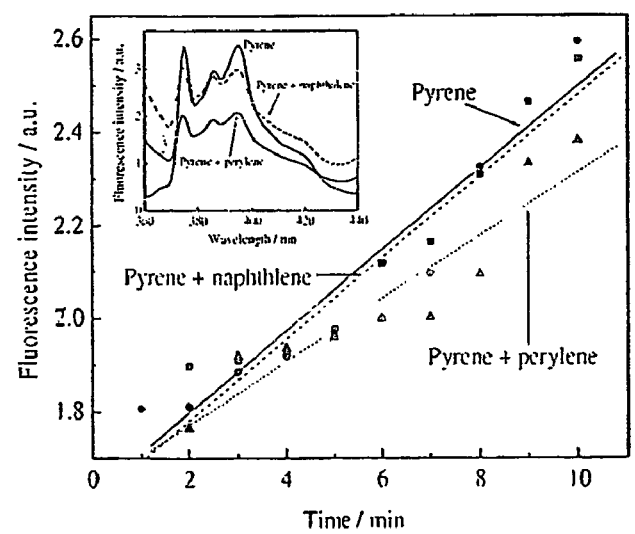
Figure 6C:
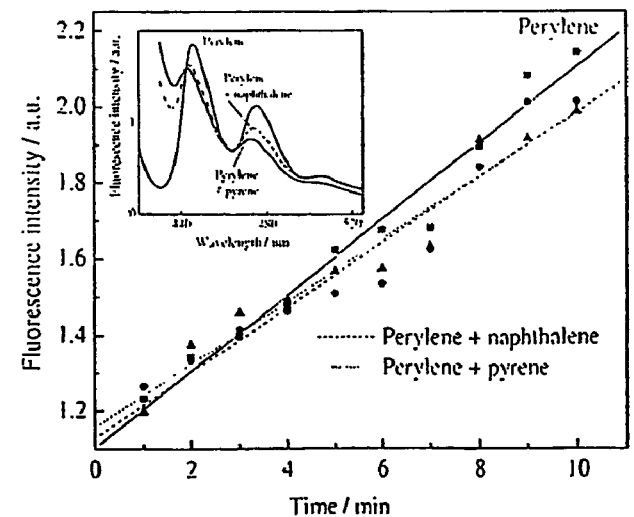

The measured fluorescence signals were compared to the data obtained for single naphthalene, pyrene and perylene sampled at the same experimental conditions. The resulting curves are provided in FIGS. 6A-6C. It is observed that the fluorescence of pyrene is not influenced by naphthalene. It is further observed that perylene slightly decreases the pyrene fluorescence signals (refer to FIG. 6B). It may therefore be concluded that the entrapping of perylene is more efficient than the entrapping of perylene to pyrene.

The spectrum is not changed by the presence of either naphthalene or perylene. Perylene signals are slightly influenced by the presence of naphthalene or pyrene (see FIG. 6C). A slight blue shift of the perylene spectrum is observed in the presence of other PAHs (see the inset of FIG. 6C). Thus, the presence of additional PAHs causes a change of the matrix influence. This effect is observed only for perylene, which is more matrix-dependent than naphthalene and pyrene. According to the data presented in FIGS. 6A-6C, the film loading by PAH mixtures is different from that by a single PAH, and some calibration for direct mixture analysis appears to be needed.

Although particulate pollutants have been identified as extremely potent carcinogens and/or mutagens, the various prior-art devices are not particularly suited to accurate sampling of particulate pollutants. We have discovered that polymeric film sensors can be appropriate for sampling and pre-concentration of airborne particulates.

Over the course of the experimental work, two kinds of aerosols were generated and analyzed. These are labeled hereafter either as type A and B. For A-type aerosols, a high-volume pump was employed to collect contaminated air inflows produced by blowing PAHs powders containing particles less than 75 μm. The particles traveled within the air flow along a 0.5 m glass tube fitted to sampler (film or filter) holder.

For B-type aerosols, the stable up-streaming flow of air supplied by a blower impacted the PAH powder. The contaminated airflow circulated in the glass bell covered from inside by film-bands arranged at the same distance from the particles source. The PAH-contaminated films or filters were extracted three times with 1.5 ml acetonitrile. The extraction efficiency was 95-98%.

The analysis of particulate perylene is based on the Fourier Transform Spectral Imaging Microscopy (FT-SIM) method. The equipment includes a fluorescence microscope, an imaging spectrometer, and detection and data processing systems. The fluorescence microscope (Axiolab, Carl Zeiss, Germany) was equipped with two UV transparent objectives. (Fluar and Ultrafluar) providing several magnifications (from ×10 and ×40). The excitation source was a variable power high-pressure mercury lamp (ABO100W/2, Carl Zeiss), attached to the microscope. Fluorescence excitation of the sample performed through the microscope objective. PAH fluorescence was excited at 365 nm using narrow-band filter (10 nm). A dichroic mirror placed in the optical path was used for cutting off the reflected light at wavelengths below 390 nm.

The microscope images were transferred to a triangular Fourier transform spectrometer (Sagnac type) and to a CCD camera (FIPA 20, Green Vision System, Israel) for simultaneous recording of the fluorescence spectra in each image pixel. The spectrometer was equipped with imaging lenses such that the full image from the microscope could be processed simultaneously.

The electrothermally-cooled CCD detector (Hamamatsu, 4880-81, Japan) was composed of up to 480×640 pixels. The CCD pixel size was 9.9×9.9 μm, which corresponds to about 1×1 μm at the object plane, when using a ×10 microscope objective, and 0.25×0.25 μm, when using a ×40 microscope objective. This chip was optimized for increased sensitivity to blue light. The imaging interferograms thus obtained were transferred to a PC for Fourier transforming, resulting in a full fluorescence spectrum at each CCD pixel. The CCD signals were digitized at 12 bits resolution. The finally obtained spectral resolution varied along the full spectral range, between 5 nm at 400 nm to 15 nm at 800 nm.

Two physical processes follow the impact of airborne particle on the surface of a polymer film. The first is the adsorption of the particle onto the surface polymer layer, and the second is the diffusion of the entrapped particle into the film bulk. The later process is comparable to solid particle dissolution into a liquid matrix.

In the FT-SIM analysis, it was found that small particles (diameter less than 1 μm) were rapidly dissolved into the film. At first, the fluorescence of each emitter was detected. The data analysis program then performed both classification and quantification of the detected compounds. The classification procedure assigned each pixel in the image to reference compounds, according to its spectral features. In this case, blue spots are observed.

Figure 7A:
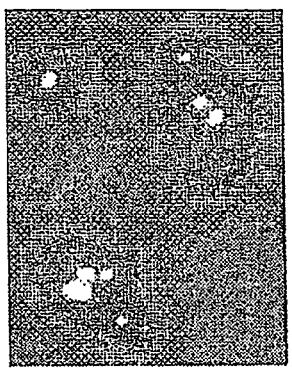
FIG. 7A is a typical FT-SIM image of film-entrapped aerosols.
Figure 7B:
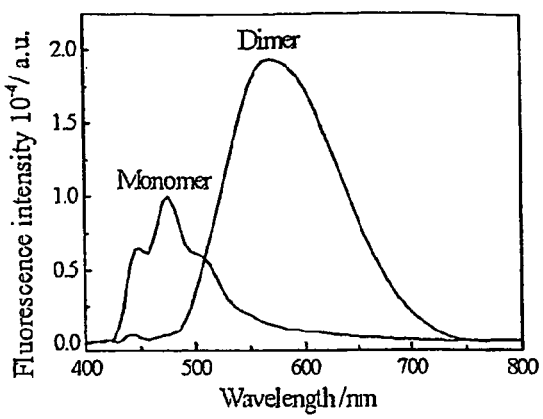
FIG. 7B provides reference fluorescence spectra of monomeric and dimeric perylene.
Figure 7C:
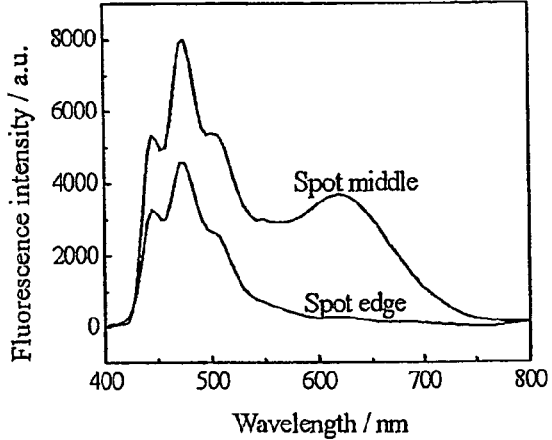
FIG. 7C shows fluorescence spectra measured at the central part of a perylene spot in the middle of the film and at the film edge.
Figure 7D:
FIG. 7D is an image providing the basis for two-dimensional classification (dimer or monomer) of the film-entrapped aerosols.
Figure 7E:
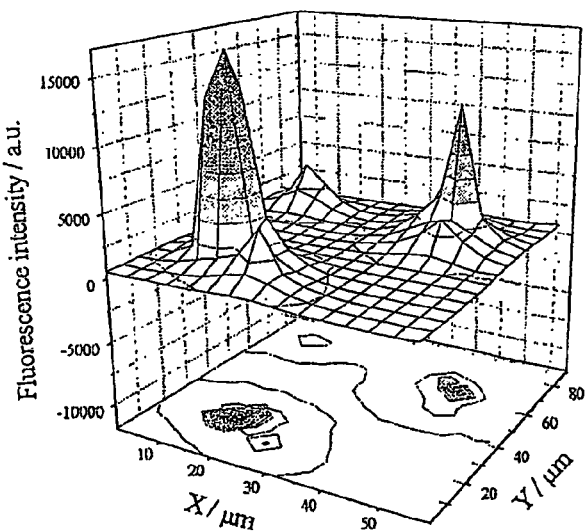
FIG. 7E is a wavelength-integrated fluorescence imaging map in which fluorescence intensities of the emitters are provided along with a contour map.

A typical image of film-entrapped aerosols is shown in FIG. 7A. Two emitter types are measured: perylene solid dimer possessing yellow fluorescence and monomer observed in the film as blue spots (in FIG. 7A perylene dimer and monomer are shown as white and gray pixels, respectively). The reference spectra of dimeric and monomeric perylene are given in FIG. 7B. Typical fluorescence emission spectra obtained from the center and the edge of the spot (refer to FIG. 7A) are shown in FIG. 7C. The spectra of the spots consist of the monomeric band of dissolved perylene. Sometimes the dimer band is also present in the middle of the spots indicating the as yet undissolved material. The fluorescence in the middle of the spot is more intense than at the edges. The smaller intensity ratio (middle to center) can be referred to continuous intra-layer diffusion of the dissolved material. After the classification procedure is completed, each identified pixel is given a different color, according to the reference compound used (see FIG. 7D). The further quantification is presented in FIG. 7E as a wavelength-integrated 3D-plot of fluorescence intensity. The peaks give the integrated fluorescence intensity and the map at the bottom displays the emitter location and size.

The penetration of perylene into the film takes place only at the film-particle interface. Thus, the dissolution of large particles deposited onto a film surface is the diffusion controlled, time-consuming process. A typical FT SIM image of a (~225 μm$^2$) perylene particle is shown in FIG. 8A. The corresponding fluorescence emission spectra obtained from the center, the edge and around of the particle are shown in FIG. 8B. The spectrum of the particle is referenced to the perylene diner and indicates a non-dissolved perylene solid situated onto the film surface. The spot surrounding the particle exhibits a monomer band indicating perylene dissolved into the film. The fluorescence spectrum measured at the particle edge is red shifted. The diffusion of PAH into the film causes destruction of crystal structure accompanied by the expansion of defects. The corresponding 3D-plot of the wavelength-integrated fluorescence intensity is shown in FIG. 8C. It can be seen that the fluorescence emission of the perylene dimer at the particle edges is higher than in the middle of the particle. The fluorescence intensity decrease toward the crystal center is attributed to self-absorption of the emitted fluorescence within the crystal. The monomer spot around the particle possess low fluorescence emission. The fluorescence intensities change as a function of time, due to particle dissolution into the film.

The fluorescence intensity emitted from particles should be related to the physical size of the crystal. The FT SIM analysis is based on surface fluorescence therefore, the measured fluorescence should be a linear function of crystal area, and we expect a linear relationship between the dimer and monomer fluorescences. However, since the particle area is detected at the plane facing of microscope objective, the crystal alignment affects the imaged fluorescence measurement. The correlation between averaged fluorescence intensity of dimer particles and corresponding monomer spots results in two sets of data, which can be attributed to two averaged crystal orientations toward the microscope objective. The most intensive dimer signals correspond to the plane crossing crystal edges (plane cut through the smallest rectangle crystal facet). The less intensive dimer signals corresponds to crystals adhering to the film by their largest facet. In this case, the fluorescence is measured at the middle of the particle.

Figure 9:
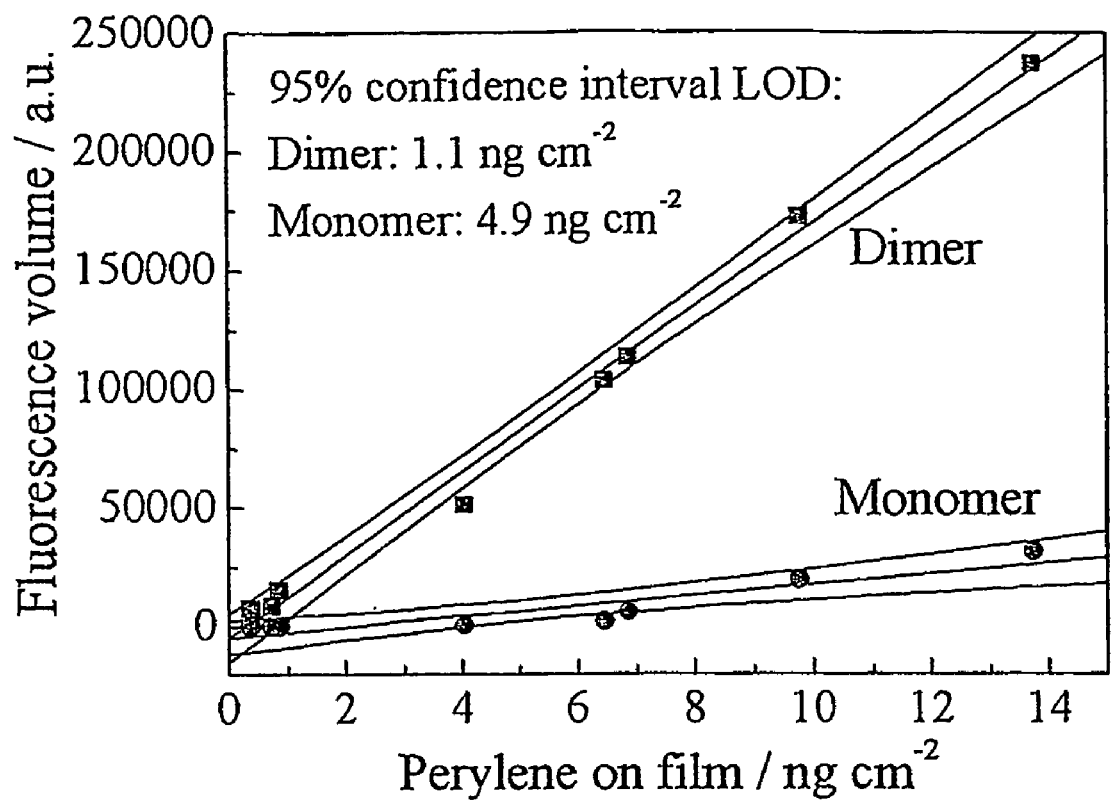
FIG. 9 is a plot of the fluorescence emission intensity of perylene dimer as a function of fluorescence emission intensity of perylene monomer, and FIGS. 10A-B provide particle size distributions of perylene sampled on a PFS (FIG. 10A) and on a glass fiber filter (FIG. 10B).

Despite the morphological and temporal effects, the spectral imaging has been found to be quite suitable for quantification of PAHs entrapped by the polymer film. The total fluorescence volume is proportional to PAH content. The integrated fluorescence intensity of perylene dimer and monomer as a function of mass entrapped by 1 $cm^2$ of film is shown in FIG. 9. The 95% confidence intervals LOD were calculated to linear regression plots in FIG. 9 and were found to be as low as 1.1 and 4.9 ng $cm^{-2}$ (of film) for dimer and monomer, respectively. The fluorescence observed in the FT SIM measurements is linearly correlated to the amount of perylene in the film. Such results validate the application of FT SIM for quantitative analysis of PAHs on a polymer film.

In addition, FT SIM analysis can provide not only the total quantitative information about the contamination but also the size distribution and particle shape. The data on aerosol size and configuration are needed for identification of the pollution source. The same total concentration can be obtained from a large number of small particles or from a small number of large crystals. However, the contamination process affects the size distribution. For example, measurements of PAHs have shown that a fresh combustion emission gives 0.01 to 0.5 μm particles, while ambient urban aerosols show a bimodal distribution with an additional group of particles in the range of 0.5 to 1.0 μm.

Figure 10A:
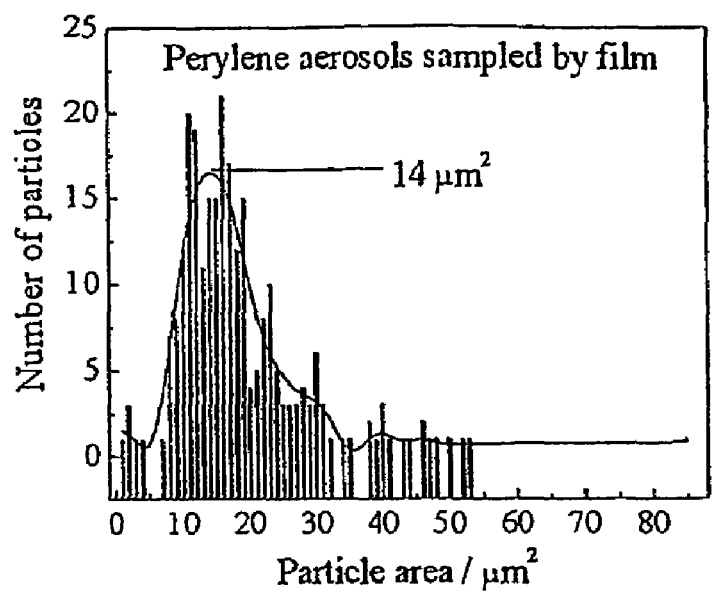
Figure 10B:
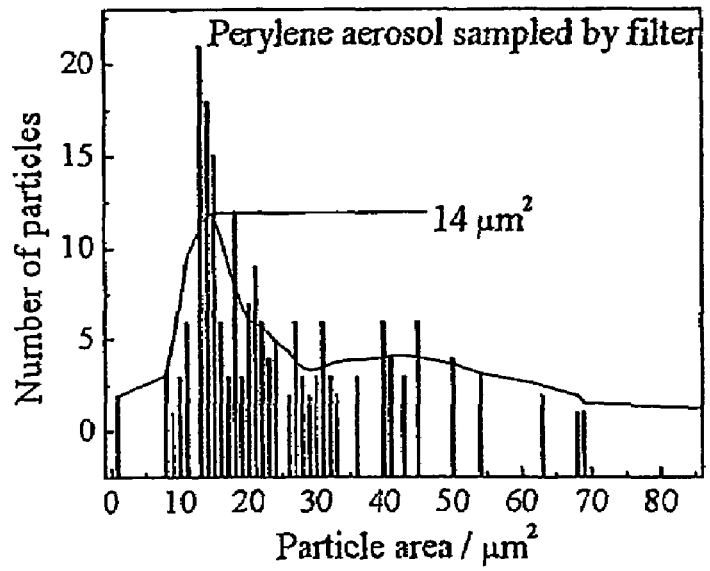

A typical size distribution for B-type perylene aerosols on a polymer film slide is provided in FIG. 10A. The sampling of perylene particles at the same conditions by a glassy-fiber filter results in the particle size distribution shown in FIG. 10B. It can be seen that at the same sampling conditions of particulates flying in a weakly turbulent stream (B-type aerosols), the total number of particles sampled by the polymer film is more than that sampled by the filter (44 particles vs. 25 particles). The most probable size was 14 $μm^2$ both for the film and for the filter, but the size distribution on the film was somewhat wider than that of the filter. In addition, polymer films entrap a wide variety of small particles; in contrast, filters mostly entrap particles larger than 7 $μm^2$. The shape of the histograms indicates that fine particles are entrapped by the film and pass through the filter.

Since most environmental particles are small, they would rapidly dissolve into the polymer film. Taking account of the above-mentioned disadvantages of FT SIM detection of perylene by the film sensor, a different analytical procedure is needed for direct analysis of small PAH particles.

Fluorescence intensity of PAHs dissolved in the film matrix can be measured, using a conventional fluorimeter equipped with a standard surface measurement accessory. Such fluorimetric measurements are sensitive to the monomer only (most solid particles giving the dimer spectrum are dissolved). The reference fluorimetric measurements of total perylene contamination were conducted using organic extracts of polymeric film sensor (OE-PFS).

Film sampling at a given flow rate was compared with that of a conventional, filter-sampling approach. Simultaneous comparison with filter-based sampling was undertaken, using double-split air stream, one influx of which was directed towards the film-sampling array, while the other was passed through a glass-fiber filter covered outlet. Fluorescence intensities measured in OE-PFS and organic extracts of the filter (OE-F) are presented in Table 1 as a function of sampling time.

It is observed that the application of film for standard high-volume sampling gives results comparable to conventional filter-based sampling. The correlation coefficient of 0.988 suggests that a reasonable correlation between the two samplers exists. Film-based sampling is, however, more sensitive: the 95% confidence interval limits of detection were 0.28 and 0.37 ng $cm^{-2}$ for film and filter-sampling, respectively. It is also observed that the extraction of the film improves the detection limit and expands the linear calibration range. Nevertheless, direct on-line and in situ measurements are feasible for environmental applications.

Selectivity tests regarding the entrapment of other, non-fluorescent particles, were performed. This is of particular importance because most ambient air pollutants are not fluorescent. The non-selective entrapping of various particles may influence sampling efficiency by films and deleteriously affect the sensitivity of the present invention. In order to qualitatively evaluate the response to the presence of small amount of insoluble dust particles, the perylene aerosols were mixed in 1:1 (by weight) ratio with quartz particulates (produced from finely ground Ottawa sand).

TABLE 1

Comparison between PFS and Filter Sampling

| Sampling time, min | Fluorescence intensity of OE-PFS | Fluorescence intensity of OE-F |
| --- | --- | --- |
| 2 | 0.137 | 0.285 |
| 5 | 0.348 | 0.310 |
| 6 | 0.349 | 0.332 |
| 7 | 0.567 | 0.614 |
| 10 | 0.662 | 0.860 |
| 15 | 1.231 | 1.358 |
| 20 | 1.685 | 1.936 |
| 30 | 2.085 | 2.472 |
| 95% confidence interval LOD, ng $cm^{-2}$ | 0.28 | 0.37 |

No significant difference in fluorescence intensity measured for film samples containing inorganic dust and pure perylene samples was observed. The OE-PFS containing inorganic dust and perylene showed the same fluorescence intensities as the perylene-only contaminated polymer film. Thus, the presence of non-fluorescent inorganic dust does not influence the PAH aerosol detection.

As used herein in the specification and in the claims section that follows, the term "transparent", in the context of a polymeric film, refers to a polymeric film that does not interfere with absorption and/or fluorescence measurements. In the case of absorption measurements, the term "transparent" means that the film is characterized by a low, preferably negligible optical interference at a spectral range in which the compounds of interest, in their adsorbed/dissolved form, possess an absorption peak. In the case of fluorescence measurements, the term "transparent" means that (a) the film has optical properties that enable excitation light (usually in the UV range), at the excitation wavelength, to reach molecules inside the film (The film should not absorb the emitted light/fluorescence, so that the light can reach the detector and is not absorbed by the medium), and (b) the polymeric film itself should not emit fluorescence at the same excitation wavelength that is used for probing the compounds of interest.

It will be readily apparent to one skilled in the art that a dedicated instrument for fast and efficient reading of the transparent polymeric cards/badges could be constructed. Such an instrument is preferably designed to pass the light through the polymeric film. A detector is disposed so as to measure the attenuation due to absorption by the molecules entrapped in the film. The light beam is diffused, such that a large portion of the film can be sampled at any given time. After passing through the film, the light beam is re-focused on the detector. A second detector is placed on the side of the light source, so as to collect the fluorescence at a given angle. An optical filter is placed between the emitted light and the second detector, in order to filter out the excitation wavelength.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A polymeric-film device for sampling solid particulates of polycyclic-aromatic-hydrocarbons (PAHs), the device comprising:

a polymeric film produced from poly(vinyl chloride-co-vinyl acetate) being transparent with respect to at least one type of said PAH, said polymeric film said polymeric film being formed from a polymer solution of the poly(vinyl chloride-co-vinyl acetate) treated with a softening agent so that said polymeric film exhibits a property of capturing suspended, solid particulates of said at least one type of PAH.

2. The device of claim 1, wherein said poly(vinyl chloride-co-vinyl acetate) contains at least 70% vinyl chloride.

3. The device of claim 1, wherein said polymeric film is configured as a badge for fastening to clothing of a subject.

4. The device of claim 3, wherein said polymeric film of said badge has a surface area for collecting the PAHs, said surface area being less than 50 square centimeters.

5. The device of claim 3, wherein said polymeric film of said badge has a surface area for collecting the PAHs, said surface area being less than 30 square centimeters.

6. The device of claim 1, wherein said polymeric film is designed and configured to be read by an analyzer selected from the group consisting of fluorescence analyzer and Fourier Transform Spectral Imaging Microscopy (FT-SIM) analyzer.

7. The device of claim 1, wherein said polymeric film is designed and configured for sampling an aerosol containing solid particulates of said at least one type of PAH.

8. The device of claim 1, wherein said polymeric film is produced from poly(vinyl chloride-co-vinyl acetate) and treated with phthalic acid bis(2-ethyl-hexyl ester) so that said poly(vinyl chloride-co-vinyl acetate) exhibits said property of capturing suspended, solid particulates of said at least one type of polycyclic aromatic hydrocarbon.

9. The device of claim 1, wherein said particulates have an area not exceeding 68 $\mu m^2$.

* * * * *

UNITED STATES PATENT AND TRADEMARK OFFICE
CERTIFICATE OF CORRECTION

PATENT NO. : 7,670,843 B2
APPLICATION NO. : 10/548068
DATED : March 2, 2010
INVENTOR(S) : Israel Schechter et al.

Page 1 of 1

It is certified that error appears in the above-identified patent and that said Letters Patent is hereby corrected as shown below:

On the Title Page item (60),

Related U.S. Application Data: Provisional application No. 60/451,661, filed on March 5, 2003 should be added.

Claim 1, Column 12, line 15 should be corrected as follows:
change
-- A polymexic-film device for sampling solid particulates of polycyclic-aromatic-hydrocarbons {PAHs), tlie device comprising:
a polymeric film produced from poly (vinyl chloride-co-vinyl acetate) being transparent with respect to at least one type of said PAH, said polymeric film said polymeric film being formed from a polymer solution of the poly (vinyl chloride-co-vinyl acetate) treated with a softening agent so that said polymeric film exhibits a property of capturing suspended, solid particulates of said at least one type of PAH. -- to

"A polymexic-film device for sampling solid particulates of polycyclic-aromatic-hydrocarbons {PAHs), tlie device comprising:
a polymeric film produced from poly (vinyl chloride-co-vinyl acetate) being transparent with respect to at least one type of said PAH, said polymeric film being formed from a polymer solution of the poly (vinyl chloride-co-vinyl acetate) treated with a softening agent so that said polymeric film exhibits a property of capturing suspended, solid particulates of said at least one type of PAH."

Signed and Sealed this

Twentieth Day of April, 2010

David J. Kappos
*Director of the United States Patent and Trademark Office*